United States Patent [19]

Heck

[11] Patent Number: 4,529,597

[45] Date of Patent: * Jul. 16, 1985

[54] SUBSTITUTED 1-AZABICYCLO(3.2.0)HEPT-6-EN-2-ONE-7-CARBOXYLIC ACIDS

[75] Inventor: James V. Heck, Fanwood, N.J.

[73] Assignee: Merck & Co., Inc., Rahway, N.J.

[*] Notice: The portion of the term of this patent subsequent to Jan. 31, 2001 has been disclaimed.

[21] Appl. No.: 369,951

[22] Filed: Apr. 19, 1982

[51] Int. Cl.³ ................. C07D 205/12; A61K 31/395
[52] U.S. Cl. ..................................... 514/413; 546/198; 544/333; 548/206; 548/202; 260/245.2 T; 260/245.2 R; 548/512; 548/515; 548/336; 514/423; 514/424; 514/375; 514/365; 514/781; 514/339
[58] Field of Search ............... 424/270, 273 R, 274, 424/251, 263, 269; 548/512, 202, 206, 336; 260/245.2 T, 245.2 R; 544/333, 3; 546/198

[56] References Cited

U.S. PATENT DOCUMENTS 4,235,917 11/1980 Christensen et al. ........ 260/245.2 T
4,235,922 11/1980 Ratfliffe et al. ............. 260/245.2 T Primary Examiner—Nicholas S. Rizzo
Attorney, Agent, or Firm—Raymond M. Speer; Hesna J. Pfeiffer

[57] ABSTRACT

Disclosed are substituted 1-azabicyclo [3.2.0]-hept-6-en-2-one-7-carboxylic acids (I) and their pharmaceutically acceptable salts and esters which are useful as antibiotics.

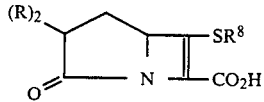

wherein R is hydrogen, and, inter alia, unsubstituted and substituted alkyl, aryl, aralkyl; $R^8$ is, inter alia, unsubstituted and substituted alkyl, alkenyl, aryl, and aralkyl. Also disclosed are processes for the preparation of such compounds; pharmaceutical compositions comprising such compounds; and methods of treatment comprising administering such compounds and compositions when an antibiotic effect is indicated.

4 Claims, No Drawings

SUBSTITUTED 1-AZABICYCLO(3.2.0)HEPT-6-EN-2-ONE-7-CARBOXYLIC ACIDS

BACKGROUND OF THE INVENTION

This invention relates to substituted 1-azabicyclo[3.2.0]-hept-6-en-2-one-7-carboxylic acids (I) and the pharmaceutically acceptable salt and ester derivatives thereof which are useful as antibiotics:

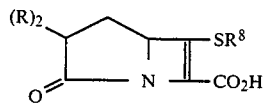

wherein R is hydrogen, and, inter alia, unsubstituted and substituted alkyl, aryl, aralkyl; $R^8$ is, inter alia, unsubstituted and substituted alkyl, alkenyl, aryl, and aralkyl. Also disclosed are processes for the preparation of such compounds; pharmaceutical compositions comprising such compounds; and methods of treatment comprising administering such compounds and compositions when an antibiotic effect is indicated.

This invention also relates to the carboxyl derivatives of I which are antibiotics and which may be represented by the following generic structure (I):

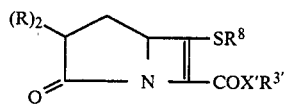

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic δ-lactam antibiotic art; $R^{3'}$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens wich representatively include both Gram positive bacteria such as *S. aureus, Strep. pyogenes,* and *B. subtillis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

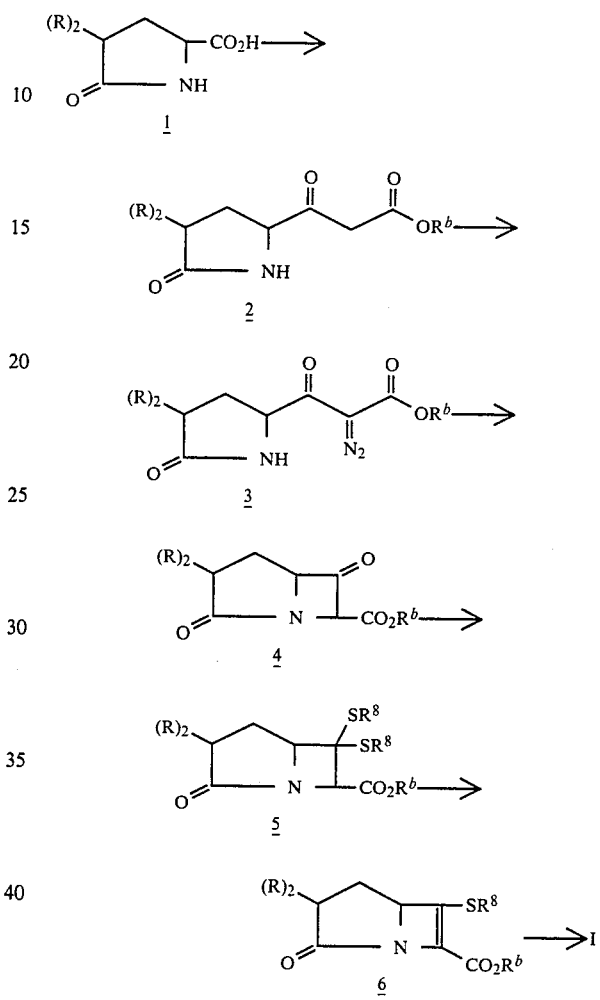

In words relative to the above diagram, the starting materials, 1, are either known (for example, R=H, 1 is pyroglutamic acid) or can be prepared according to procedures described below. An especially preferred class of compounds I of the present invention is when the 3-substituent of I, above, is $CH_3CH(OH)$—. An example describing the preparation of starting material 1 when $R=CH_3CH(OH)$ is given below.

The addition 1 to 2 is accomplished by treating 1 with 1,1'-carbonyldiimidazole, or the like, in a solvent such as tetrahydrofuran, dimethoxyethane, or the like, at a temperature of from 0° to 50° C., followed by the addition of 1.1 to 3.0 equivalents of $(R^bO_2CCH_2CO_2)_2Mg$, at a temperature of from 0° to 50° C. for from 1 to 48 hours. $R^b$ is a readily removable carboxyl protecting group such as p-nitrobenzyl, benzyl, or the like.

The diazo species 3 is prepared from 2 by treating 2 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as thiethylamine, pyridine, $(C_2H_5)_2NH$, or the like, for from 1 to 50 hours at 0°–25° C.

Cyclization (3-4) is acomplished by treating 3 in a solvent such as benzene, toluene, THF, or the like, at a temperature of from 50°–110° C. for from 1–5 hours in the presence of a catalyst such as bis (acetylacetonato)-CU(II) [Cu(acac)$_2$], CuSO$_4$, Cu powder, Rh(OAc)$_2$ or Pd(OAC)$_2$. Alternatively, the cyclization may be accomplished by irradiating 7 through a pyrex filter (a wave length greater than 300 nm) in a solvent such as benzene, CCl$_4$, diethylether, or the like, at a temperature of from 0°–25° C. for from 0.5 to 2 hours. ["OAc"- = acetate.]

The transformation 4 to 5 is accomplished by treating 4, in a solvent such as THF, acetonitrile, or the like, with 1.0 equivalent of a strong base such as 1,8-diazabicyclo[5.4.0]undec-7-ene (DBU), or 1,5-diazabicyclo[4.3.0]non-5-ene (DBN), in the presence of ($\phi$O)$_2$POCl, (EtO)$_2$POCl, or tosyl chloride, followed by treating with the reagent R$^8$SH in the presence of 2.0 to 2.5 equivalents of a base, such as, diisopropylethylamine, or triethylamine, or the like. R$^8$ is as defined above. Representative values of R$^8$, expressed in the form of the reagent HSR$^8$, expressed in the form of the reagent HSR$^8$, are given below.

The dithioketal 5 is converted to 6 on treatment with an oxidizing agent, such as m-chloroperbenzoic acid, peracetic acid, perbenzoic acid, or the like, followed by treatment with 1.0 to 1.2 equivalents of a strong base such as 1,8-diazabicyclo[5.4.0]undec-7-ene (DBU), or 1,5-diazabicyclo[4.3.0]non-5-ene (DBN). Suitable solvents for the transformation 5 to 6 include dichloromethane, THF, ether, or the like. Typically the reaction is conducted at 20' to 40° C. for from 1 to 2 hours. (THF is tetrahydrofuran.)

The final deblocking step 6 to I is accomplished by conventional procedures such as hydrolysis or hydrogenation. Typically 6, in a solvent such as dixane-water-ethanol, tetrahydrofuran-aqueous dipotassium hydrogen phosphate-isopropanol, or the like, is treated under a hydrogen pressure of from 1 to 4 atmospheres in the presence of a hydrogenation catalyst such as palladium on charcoal, palladium hydroxide, or the like, at a temperature of from 0° to 50° C., for from 0.5 to 4 hours to provide I.

As noted above, the compounds of the present invention may also generally be represented by the following structural formula:

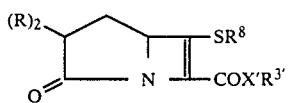

wherein X' is oxygen, sulfur or NR' (R' is hydrogen or loweralkyl having from 1 to 6 carbon atoms); and R$^{3'}$ is hydrogen, or, inter alia, is representatively selected to provide the pharmaceutically acceptable salt, ester, anhydride (R$^{3'}$ is acyl), and amide moieties known in the bicyclic β-lactam antibiotic art; R$^{3'}$ may also be a readily removable blocking group.

Identification of the Radical —COX'R$^{3'}$

In the generic representation of the compounds of the present invention (I, above), the radical represented by —COX'R$^{3'}$ is , inter alia, —COOH (X' is oxygen and R$^{3'}$ is hydrogen) and all radicals known to be effective as pharmaceutically acceptable ester, anhydride (R$^{3'}$ is acyl) and amide radicals in the bicyclic β-lactam antibiotic art, such as the cephalosporins and penicillins and nuclear analogues thereof.

Suitable, but representative, blocking esters R$^{3'}$ (X=O) include those selected from the following list which is representative:

(i) R$^{3'}$=CR$^a$R$^b$R$^c$ wherein at least one of R$^a$, R$^b$, and R$^c$ is an electrondonor, e.g., p-methoxyphenyl. The remaining R$^a$, R$^b$ and R$^c$ groups may be hydrogen or organic substituting groups. Suitable ester groups of this type include p-methoxybenzyloxycarbonyl.

(ii) R$^{3'}$=CR$^a$R$^b$R$^c$ wherein at least one of R$^a$, R$^b$ and R$^c$ is an electron-attracting group, e.g., p-nitrophenyl, trichoromethyl, and o-nitrophenyl. Suitable esters of this type include p-nitrobenzyloxycarbonyl, and 2,2,2-trichloroethoxycarbonyl.

(iii) R$^{3'}$=CR$^a$R$^b$R$^c$ wherein at least two of R$^a$R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: R$_3^4$SiX' wherein X' is a halogen such as chloro or bromo and R$^4$ is alkyl, having 1-6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R$^{3'}$ group at the 3-position; wherein X' is oxygen, sulfur or NR'(R' is H or R$^{3'}$), and R$^{3'}$ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkylportion has 1–6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1–4 carbon atoms such, as 2-propenyl, 3-butenyl, and 4-butenyl; aralkyl and lower alkoxyl- and nitro- substituted aralkyl such as benzyl, benzhydryl, o-nitrobenzyl, p-methoxybenzyl, and p-nitrobenzyl; phthalidyl; benzyloxyalkyl having 8–10 carbon atoms such as benzyloxymethyl, and (4-nitro) benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R$^{40}$ radicals of the present invention are those wherein (relative to Structure I above), X' is oxygen and R$^{3'}$ is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

Preparation of Starting Material 1

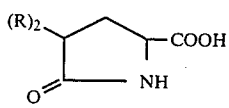

1

Relative to starting material 1, the R substituent is established by treating a suitably protected derivative of S-pyroglutamic acid such as acetonide 3a with an alkylating or acylating agent designed to establish the R group of choice:

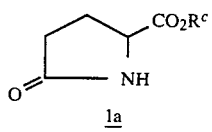

1a

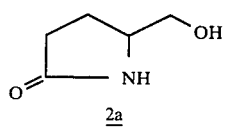

2a

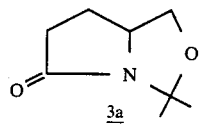

3a

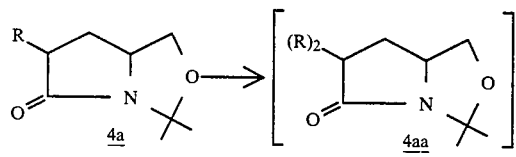

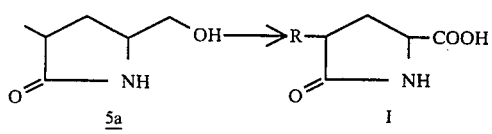

In words relative to the above diagram, 1a is reduced to 2a by treating 1a in a solvent such as ethanol, methanol, or the like, with a reducing agent, such as NaBH₄, KBH₄, LiBH₄, or the like, at a temperature of from 0° to 30° C. for from 1 to 4 hours. Relative to structure 1a, $R^c$ in $C_1$-$C_6$ alkyl, aryl or aralkyl having 6–13 carbon atoms.

The transformation 2a to 3a, provides protected intermediate 3a for subsequent reactive steps. While other schemes of protection are appropriate, the above illustration is typical. Here, 2a in a solvent such as benzene, toluene, or the like, is treated with 1 to 1.5 equivalents of 2,2-dimethoxypropane and catalytic tosic acid at a temperature of from 80° to 110° C. for from 4 to 24 hours to provide 3a.

Alkylation of 3a provides 4a. Typically, 3a is treated with a strong base such as lithium diisopropylamide, lithium 2,2,6,6-tetramethylpiperidide, potassium hydride, lithium hexamethyldisilazane, phenyllithium or the like in a solvent such as tetrahydrofuran (THF), hexamethylphosphoramide, ether, dimethoxyethane, and the like at a temperature of from −80° C. to 0° C. whereupon the alkylating agent of choice, RX° is added (X° is chloro, iodo or bromo); alternatively the alkylating agent may be R-tosylate, R-mesylate or an aldehyde or ketone such as acetaldehyde to provide monoalkylated species 4a. When desired, dialkylated species 4aa may be obtained from 4a by repeating the alkylating procedures 3a to 4a.

The eventual 3-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing R (and R,R).

The following list is representative of useful alkylating agents for establishing R (and R,R) according to the above scheme.

Alkylating Agents
CH₃CHO
φCH₂CHO  φ = phenyl
φCH₂CH₂CHO
CH₂O
CH₃I
φCH₂Br
CH₃COCH₃

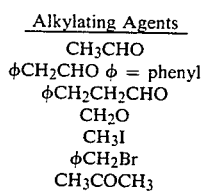

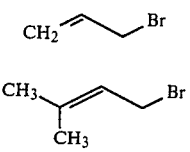

CH₃OCH₂CHO
CH₃CH₂I
(CH₃)₂CHI
N₃CH₂CHO
(CH₃)₂NCH₂CHO
RO₂CCH₂Br R = CH₃, benzyl, p-nitrobenzyl
CF₃CF₂CHO
RO₂CCH₂CHO R = CH₃, benzyl, p-nitrobenzyl
CH₃CH(CH₃)CHO,
CH₃(CH₃)CHCH₂CHO,
CH₃CH₂CHO,

,

CF₃CHO,

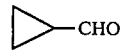

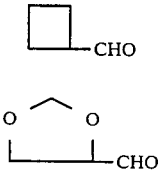

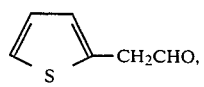

-continued
Alkylating Agents

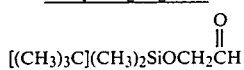

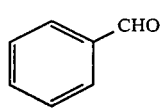

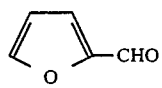

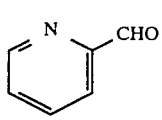

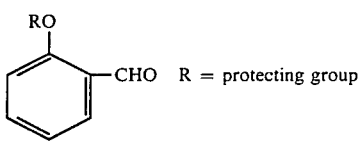 R = protecting group

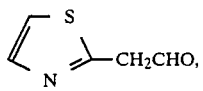

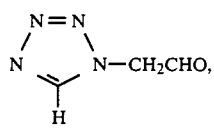

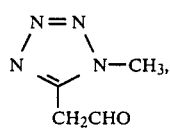

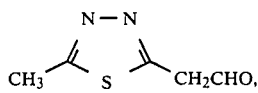

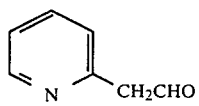

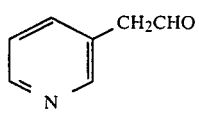

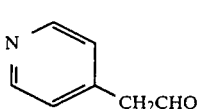

-continued
Alkylating Agents

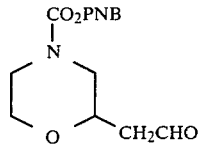

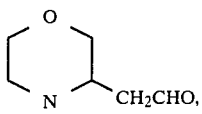

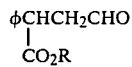

R is removable carboxyl protecting group, such as benzyl.

As mentioned above, the 3-substituents may also be established by acylation. Utilization of such acylating agents may be demonstrated in the following manner with regard to a preferred starting material 1.

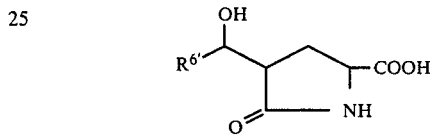

wherein $R^{6'}$ is defined relative to the definition of R and in that sense is the balance of the previously identified group R. In other words, for purposes of this definition, $R^{6'}CH(OH)—=R$. An especially preferred material is the illustrated mono-substituted species. Basically, such 1'-hydroxy $R^{6'}$ species 1 are prepared according to the following scheme:

SCHEME II

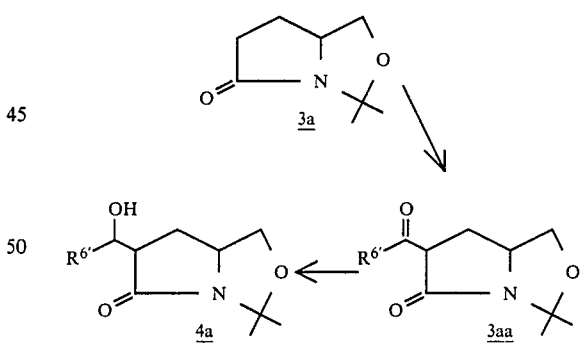

The alkylation 3a to 4a is accomplished as previously described, by treating 3a in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde.

Intermediate 3a may proceed directly to 4a as indicated above, or it may take the circuitous path via 3aa. The direct acylation, to 3aa is accomplished by treating 3a with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acyl imidazole or the like. Addition of the 3a plus base mixture to the acylating agent is preferred.

Representative acylating agents for this scheme 3a to 3aa to 4a are listed below:

$$\underset{\|}{\overset{O}{RC}}-N\underset{\diagup}{\diagdown}N\; ; R=CH_3, ClCH_2, CH_3CH_2, N_3CH_2, CH_3OCH_2,$$

[phenyl-CH$_2$–, cyclopropyl-CH$_2$–, cyclopropyl-CH$_2$– with double bond, thiazolyl-CH$_2$–]

$$\underset{\|}{\overset{O}{RC}}-SCH_2CH_3; R=CF_3, CF_2H, CH_2=CH, \text{cyclopropyl},$$

[phenyl, furyl]

Further with respect to this second acylation scheme, the reduction, 3aa to 4a is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene, i-propanol or the like at a temperature of from −78° to 25° C. The reaction can conveniently be conducted in the presence of an added complexing salt such as potassium iodide, magnesium bromide or the like.

Now, returning to the above alkylation/acylation scheme, the resulting intermediate 4a (or 4aa) is deprotected by hydrolysis to 5a. Typically this transformation (4a to 5a) is accomplished by heating 4a in aqueous methanol, or the like, with Dowex-50 H+ for from 1 to 3 hours at 40° to 60° C.

Oxidation of 5a provides 6a. Typically 5a in a solvent such as ether, dichloromethane, acetic acid, or the like, is treated with an oxidizing agent such as Jones' reagent (chromic acid).

Preferred values of R carry a hydroxyl group. Such groups are ideally protected with an acyl covering group $$\underset{\|}{\overset{}{R'OC-}}\\O$$

at the 4a level. Suitable reagents for establishing the O-protecting group $$\underset{\|}{\overset{}{R'OC-}}\\O$$

include: p-nitrobenzyl chloroformate, o-nitrobenzyl chloroformate, and the like. Typically, such protecting groups are established by treatment of 4a with a chloroformate and 4-dimethylaminopyridine in dichloromethane, chloroform or the like.

Definition of $R^8$, $HSR^8$ $R^8$ is independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl, wherein the heteroatom or atoms are selected from O, S, N: wherein the substituent or substituents relative to the above-named radical $R^8$ are selected from the group consisting of:

—X° halo (chloro, bromo, fluoro)

—OH hydroxy

—OR$^1$ alkoxy, aryloxy $$-\underset{\|}{\overset{O}{O}}CNR^1R^2 \text{ carbamoyloxy}$$

$$-\underset{\|}{\overset{O}{C}}NR^1R^2 \text{ carbamoyl}$$

—NR$^1$R$^2$ amino $$-N-R^1-\underset{|}{\overset{R^2}{C}}=NR^1 \text{ amidino}$$

$$-N-R^1-\underset{|}{\overset{NR^1R^2}{C}}=NR^1 \text{ guanidino}$$

—SO$_2$NR$^1$R$^2$ sulfamoyl $$-NH\underset{\|}{\overset{O}{C}}NR^1R^2 \text{ ureido}$$

$$NR^1\underset{\|}{\overset{O}{C}}R^2 \text{ amido}$$

—CO$_2$H carboxy

—OSO$_3$R$^1$ sulphate

—NO$_2$ nitro

—N(R$^1$)$_3^+$ ammonium (R$^1$ groups independently chosen)

$$-\underset{|}{\overset{R^1}{C}}=NOR^2 \text{ oximino}$$

—CO$_2$R$^1$ carboxylate $$-\underset{\|}{\overset{O}{C}}R^1 \text{ acyl}$$

$$-O\underset{\|}{\overset{O}{C}}R^1 \text{ acyloxy}$$

—SH mercapto $$-\underset{\|}{\overset{O}{S}}R^1 \text{ alkyl and aryl sulfinyl}$$

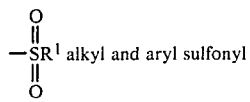 alkyl and aryl sulfonyl

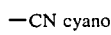 cyano

 azido

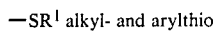 alkyl- and arylthio

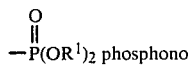 phosphono

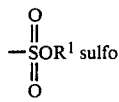 sulfo

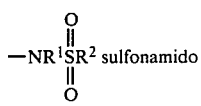 sulfonamido wherein, relative to the above listed substituents on $R^6$, $R^7$, and $R^8$, the groups $R^1$ and $R^2$ are independently selected from: hydrogen, alkyl, alkenyl, and alkynyl, having from 1-10 carbon atoms; cycloalky, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroalkyl, heteroaralkyl, heterocyclyl and heterocyclylalkyl and wherein the hereto atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms.

Further, relative to $R^8$, radicals which carry an amino group ($-NH_2$) or an N-substituted amino group ($-NR^1H$), and which can be represented conveniently as: $-R^8-NH_2$, and $-R^8-NR^1H$, respectively, there exists the following groups classed under previously defined $R^8$:

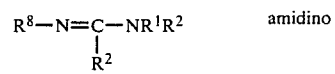 amidino

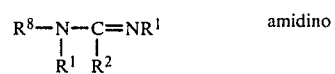 amidino

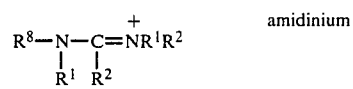 amidinium

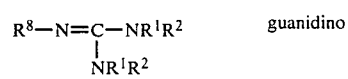 guanidino

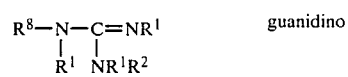 guanidino

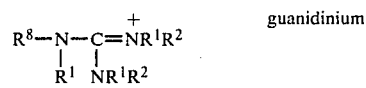 guanidinium

$HSR^8$ REAGENTS

Relative to the foregoing description of the invention, suitable reagents, $HSR^8$, which are utilized in the transformation 4 to 5 are listed below. The list is arranged according to structural and functional characteristics of this side chain $-SR^8$; anotation is provided where necessary. It should be noted tha only $HSR^8$ reagents are expressly shown. The thia side chain of choice $-SR^8$ is derived from the corresponding mercaptan reagent $HSR^8$, and thus the following list serves to further, specifically disclose $-SR^8$ side chains of I which are of special interest. When the mercaptan contains a functional group which might interfere with the intended course of reaction, the offending group is covered. For example, when a basic nitrogen group is encountered ($-NHR$ or $-NH_2$, for example) it is usually protected by acylation (e.g., $-CO_2PNB$) and when a carboxyl group ($-CO_2H$) is present, it is usually protected by esterification (e.g., PNB ester). Such protection also facilitates in the purification of products by chromatographic means. (PNB is p-nitrobenzyl). Such protection is, however, not a necessary requirement for introduction of the $-SR^8$ side chain.

It is recognized that $SR^8$ side chains in which the $R^8$ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved $-SR^8$ side chains.

1. Aliphatic Mercaptans:

$HSR^8$ wherein $R^8$ is 1-10 carbon alkyl, cycloalkyl, alkenyl, cycloalkenyl, or alkynyl; $R^8$ may be branched or unbranched, Examples
$HSCH_3$
$HSCH_2CH_3$
$HSCH_2CH_2CH_3$
$HSCH(CH_3)_2$
$HS(CH_2)_3CH_3$

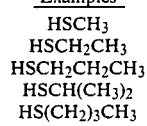

$HSCH_2CH(CH_3)_2$

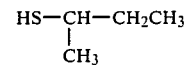

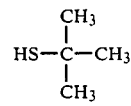

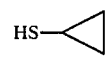

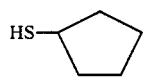

-continued
Examples

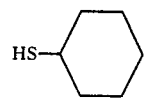

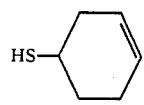

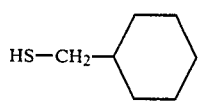

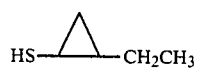

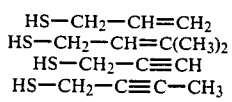

HS—CH$_2$—CH=CH$_2$
HS—CH$_2$—CH=C(CH$_3$)$_2$
HS—CH$_2$—C≡CH
HS—CH$_2$—C≡C—CH$_3$

2. Substituted Aliphatic Mercaptans:

HSR$^8$ wherein R$^8$ is a 1-10 carbon branched or unbranched alkyl, cycloalkyl, alkenyl, cycloalkenyl, or alkynyl group substituted by one or more halo,

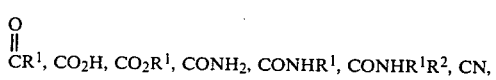

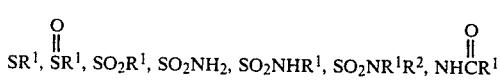

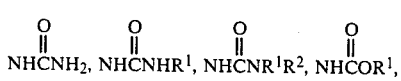

wherein R$^1$ and R$^2$ are as previously defined relative to substituents on R$^8$. Preferred substituents are basic nitrogen-containing groups.

EXAMPLES

| | |
|---|---|
| HS(CH$_2$)$_n$OR$^1$ | n = 2-4, R$^1$ = H, $\overset{O}{\overset{\|}{C}}$CH$_3$, CH$_3$ |
| HS(CH$_2$)$_n$$\overset{O}{\overset{\|}{C}}$XR | n = 1-3, X = O, NH, NR$^1$; R$^1$ = H, CH$_3$ |
| HS(CH$_2$)$_n$NH$_2$ | n = 2-4 |
| HS(CH$_2$)$_n$NHR$^1$ | n = 2-4, R$^1$ = CH$_3$, CH$_2$CH$_3$, CH$_2$CH$_2$CH$_3$, $\overset{O}{\overset{\|}{C}}$CH$_3$ |
| HS(CH$_2$)$_n$NR$^1$R$^2$ | n = 2-4, R$^1$/R$^2$ = CH$_3$, CH$_2$CH$_3$ |
| 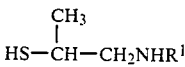 | R$^1$ = H, CH$_3$, $\overset{O}{\overset{\|}{C}}$CH$_3$ |
| 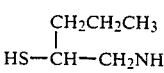 | |

-continued
EXAMPLES

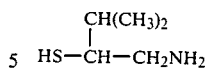

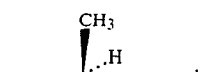    R$^1$ = H, CH$_3$

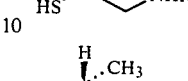

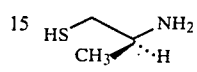

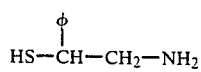

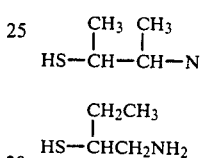

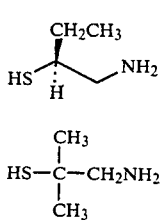

HS—CH$_2$CH$_2$SCH$_3$

HS—CH$_2$CH$_2$NHC(CH$_3$)$_3$

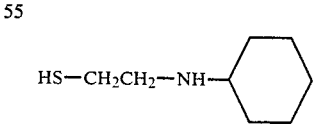    R$^1$ = H, CH$_3$, $\overset{O}{\overset{\|}{C}}$CH$_3$

HS—CH$_2$CH$_2$—NH—⌬

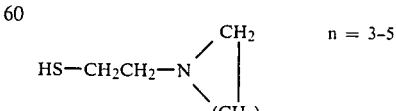    n = 3-5

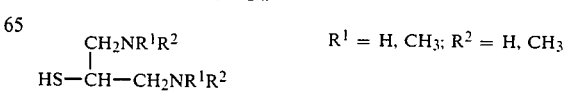    R$^1$ = H, CH$_3$; R$^2$ = H, CH$_3$

-continued
EXAMPLES
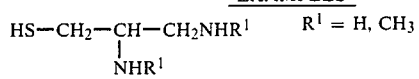 R¹ = H, CH₃
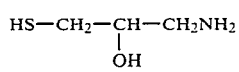
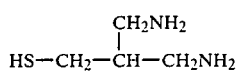
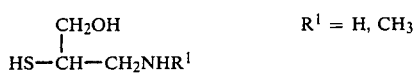 R¹ = H, CH₃
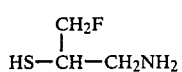
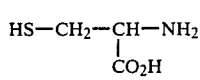
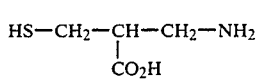
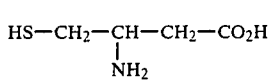
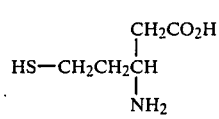
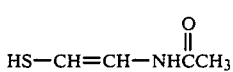
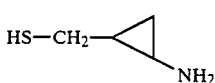
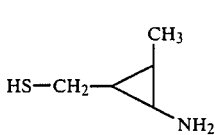
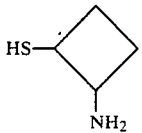
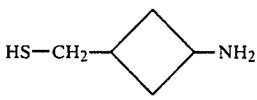
-continued
EXAMPLES
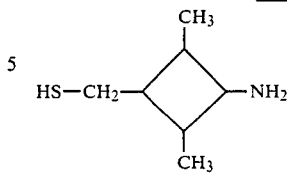
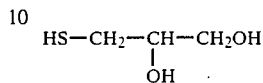
5-thio-D—glucose
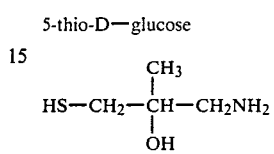
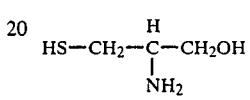
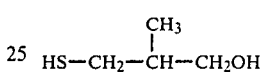
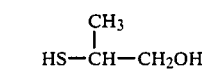
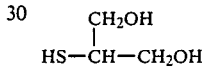
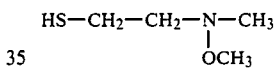
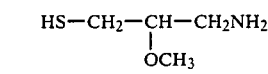
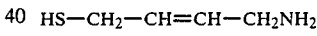
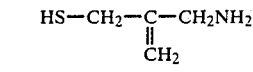
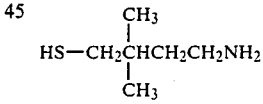
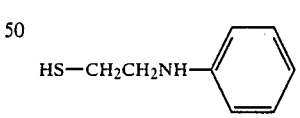
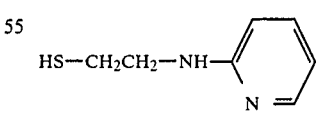
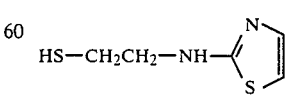
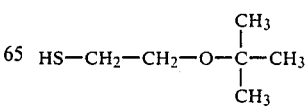

3. Aryl Mercaptans:

HSR$^8$ wherein R$^8$ is phenyl or substituted phenyl. The substituents are independently selected from those previously defined for R$^8$. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

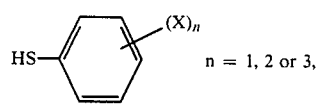

n = 1, 2 or 3,

X = F, Cl, Br, OH, OR, O$\overset{\overset{O}{\|}}{C}$R$^1$, NH$_2$,

NHR$^1$, NR$^1$R$^2$, CH$_2$NH$_2$, CH$_2$NR$^1$R$^2$, CO$_2$H, CO$_2$R$^1$, COR$^1$, CONH$_2$, CONR$^1$R$^2$, R$^1$CONH,

R$^1$NHCONH, SR$^1$, $\overset{\overset{O}{\|}}{S}$R$^1$, SO$_2$R$^1$, CH$_3$, CF$_3$;

R$^1$ and R$^2$ are as previously defined under R$^8$.

Examples

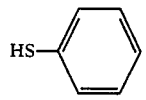
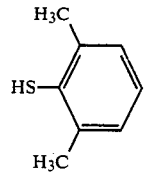
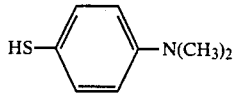
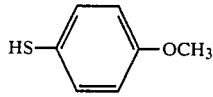
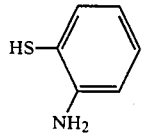
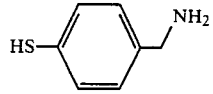
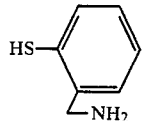
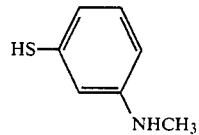
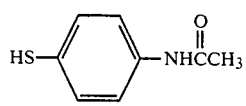

-continued
Examples

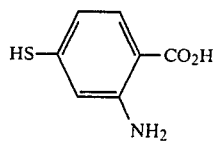

4. Heteroaryl Mercaptans:

HSR$^8$ wherein R$^8$ is a substituted or unsubstituted heteroaryl group containing 1–4 O, N or S atoms. Typical substituents include those mentioned above under "Aryl Mercaptans".

Examples

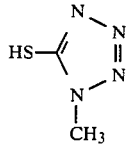
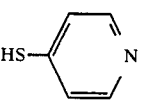
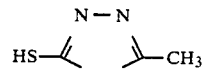
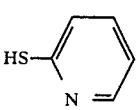

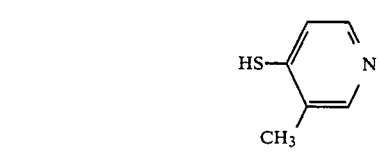

X = N,O  Y = H
X = S    Y = H, Cl, OCH$_2$CH$_3$

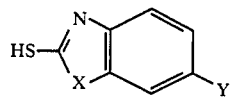
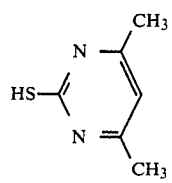
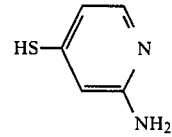

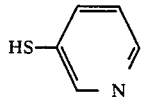

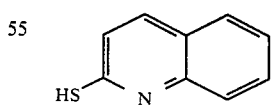

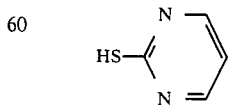

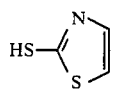

-continued

Examples
R = H, CH₃

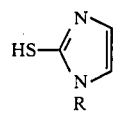

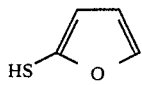

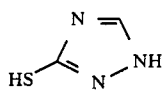

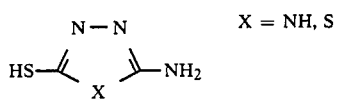

X = NH, S

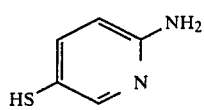

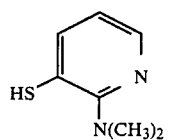

5. Arylaliphatic Mercaptans:

HSR⁸ where R⁸ is a 1-6 carbon branched or unbranched alkyl, cycloalkyl, alkenyl, or alkynyl group substituted by a phenyl or substituted phenyl group. Typical phenyl substituents include those mentioned under "Aryl Mercaptans".

Examples

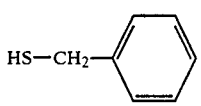

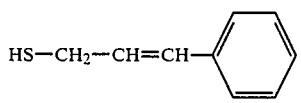

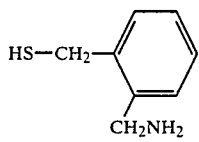

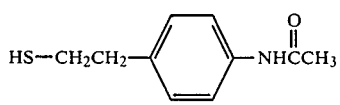

6. Heteroarylaliphatic and Heterocyclylaliphatic, and heterocyclic Mercaptans

HSR⁸ wherein R⁸ is a 1-6 carbon branched or unbranched alkyl, cycloalkyl, alkenyl, or alkynyl group substituted by a heteroaryl or heterocyclyl group containing 1-4, O, N, or S atoms. The heteroaryl or heterocyclic group is unsubstituted or substituted by those substituents mentioned under "Aryl Mercaptans", (No. 3 above).

Examples

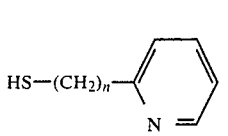

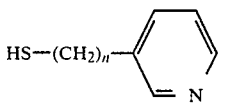

n = 1,2

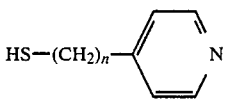

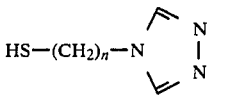

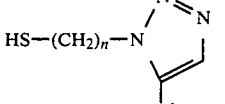

R¹ = OCH₂CH₃

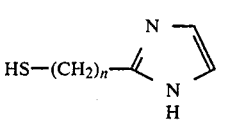

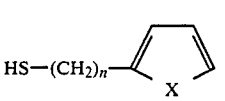

X = O, S, NH

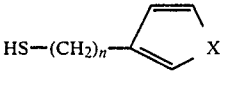

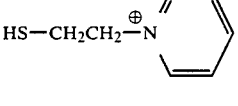

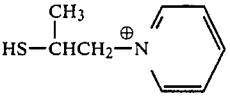

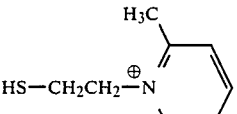

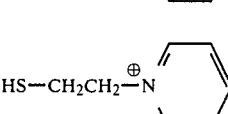

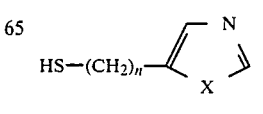

X = O, S, NH

-continued

Examples

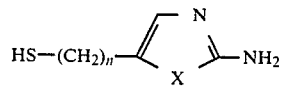 X = O, S, NH

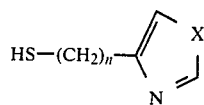 X = O, S, NH

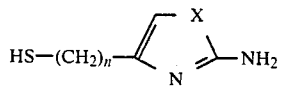 X = O, S, NH

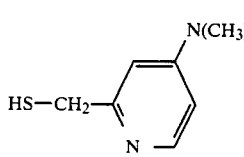

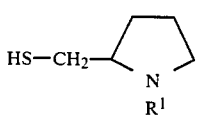 $R^1$ = H, CH$_3$

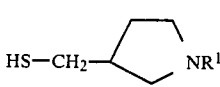 $R^1$ = H, CH$_3$

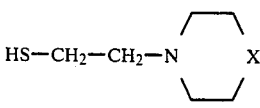 X = O, NH, NCH$_3$

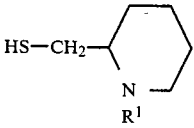 $R^1$ = H, CH$_3$

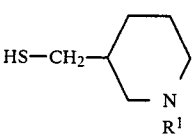 $R^1$ = H, CH$_3$

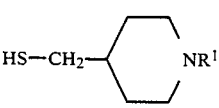 $R^1$ = H, CH$_3$

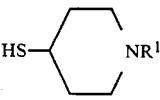 $R^1$ = H, CH$_3$

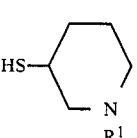 $R^1$ = H, CH$_3$

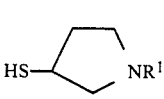 $R^1$ = H, CH$_3$

-continued

Examples

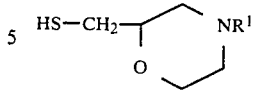 $R^1$ = H, CH$_3$

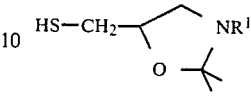 $R^1$ = H, CH$_3$

7. Alkyl-Heteroatom-Alkyl Mercaptans, HSR$^8$

Wherein R$^8$ is —(CH$_2$)$_n$X(CH$_2$)$_m$R$^9$ wherein n=2 to 4, m=2 to 4; X is NR°, O or S; and wherein R° is H, CH$_3$, CH$_2$CH$_3$, CH$_2$CH$_2$OH, or CH$_2$CH$_2$NH$_2$ and R$^9$ is OH, NH$_2$, NHCH$_3$, N(CH$_3$)$_2$, $$\underset{O}{\overset{\|}{O}}CCH_3, \underset{O}{\overset{\|}{N}}HCCH_3.$$

Note, in the above representation, the methylene carbons may be branched; for example:

and the like.

The following HSR$^8$ are representative of this class:

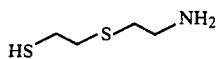  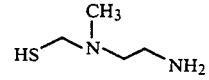

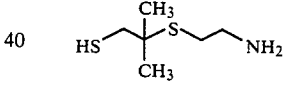  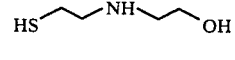

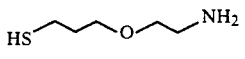  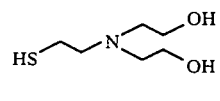

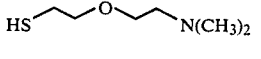  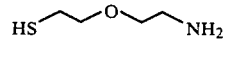

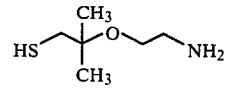

8. Amidino and Amidinium Mercaptans HSR$^8$

Wherein R$^8$ is:

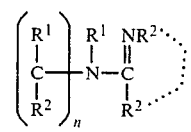

-continued

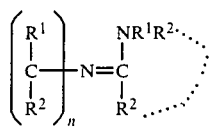

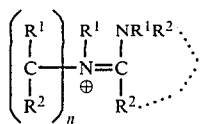

and wherein n=2-6; $R^1$ and $R^2$ are as initially defined under $R^8$; and the dotted line indicates provision for the ring formed by the joinder of substituents carried by the imino carbon atoms. Such amidino and amidinium embodiments of final products I are also conveniently obtained by N-derivatization of the corresponding amino embodiment I according to the procedure disclosed in U.S. Pat. No. 4,194,047 which patent is incorporated herein by reference since the N-derivatization of thienamycin disclosed in the incorporated by reference patent is strictly analogous to the N-derivatization contemplated to achieve the amidino embodiments characterized herein.

The following reaction summarizes such N-derivatization:

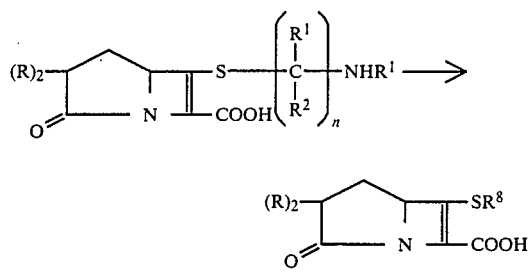

wherein: $R^8$ is defined above in this category No. 8.

Relative to the amidino embodiments characterized under this heading, representatively preferred values for $R^1$ and $R^2$ attached to the carbon atom include:
H,
CH₃,
CH₂CH₃,
CH₂OH,
OCH₃,
CH₂NH₂,
F,
phenyl,
CF₃,
CH(CH₃)₂,
CH₂CH₂CH₃,
CH₂F
benzyl, SCH₃, N(CH₃)₂, N⁺(CH₃)₃X⁻ (X⁻ defined above)

Representatively preferred values for $R^1$ and $R^2$ attached to the nitrogen atoms include:
H, phenyl, CH(CH₃)₂, C(CH₃)₃, NH₂,
CH₃, NHCH₃, N(CH₃)₂,
CH₂CH₃,
CH₂CH₂OH,
—(CH₂)₄—,
—CH₂CH₂—O—CH₂CH₂,
OCH₃

Representatively preferred values for $R^2$ attached to the imino carbon atom include:
H,
CH₃,
CH₂CH₃,
phenyl The following values for HSR⁸ are also classified under the amidino mercaptans, giving rise to amidino embodiments of I:

$R^8$ is:

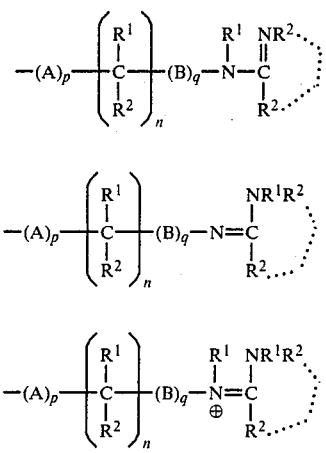

wherein $R^1$, $R^2$ and n are as defined immediately above; p and q are 0 or 1; A and B are selected from: the aforementioned values for $R^8$ expressed in bivalent form (—$R^8$—) from categories Nos. 1-7; thus, A and B (or —$R^8$—) are selected from: cycloalkyl, alkenyl, cycloalkenyl, alkynyl (see Class No. 1 above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); aryl aliphatic (see Class No. 5, above); heteroarylaliphatic, heterocyclyaliphatic, and heterocyclic (see Class No. 6, above); and alkylheteroatom-alkyl (see Class No. 7, above); and B can also be selected from —O— and —$NR^1$—.

EXAMPLES

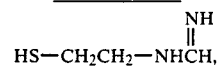

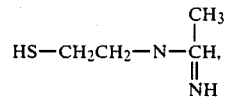

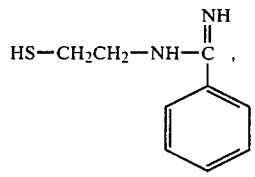

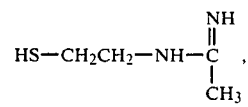

-continued
EXAMPLES
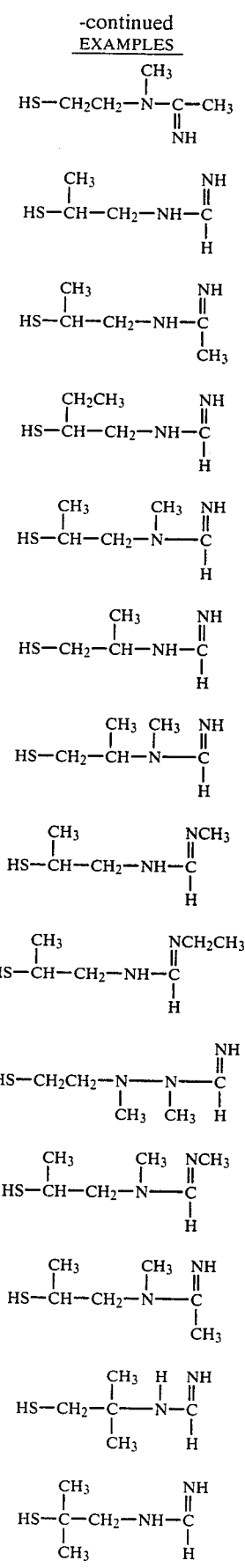
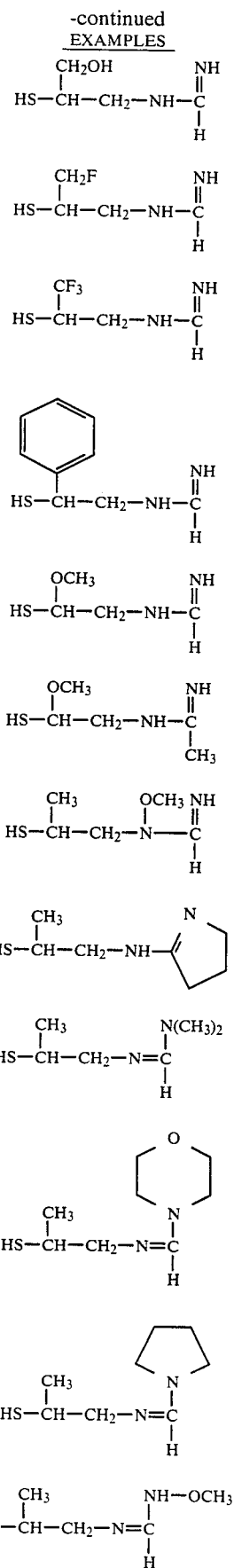

-continued
EXAMPLES

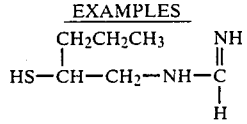
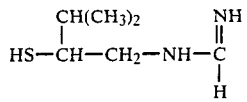
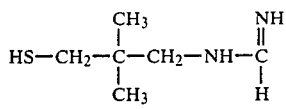
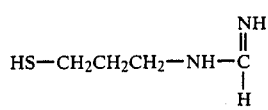
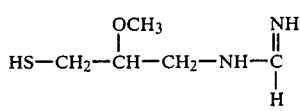
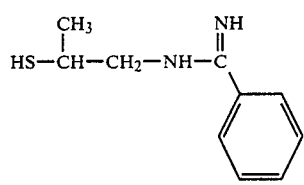
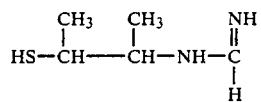
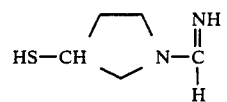
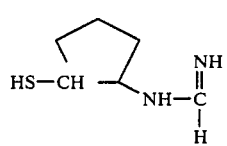
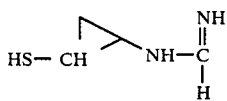
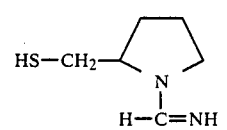
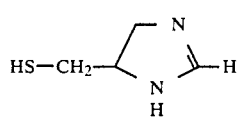
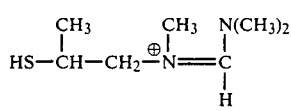

-continued
EXAMPLES

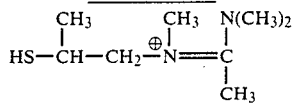
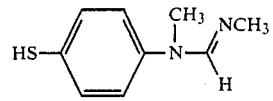
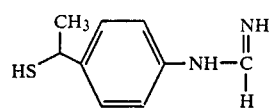
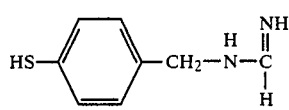
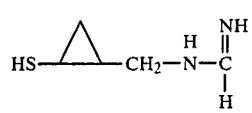
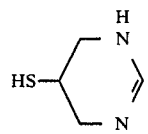
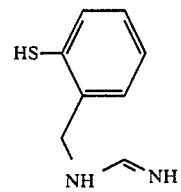

9. Guanidino and Guanidinium Mercaptans $HSR^8$ Wherein $R^8$ is:

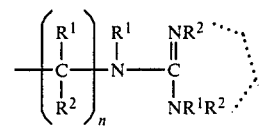
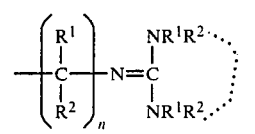
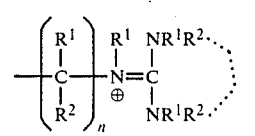

and wherein n=2–6; $R^1$ and $R^2$ are as initially defined under $R^8$; and the dotted line indicates provision for the ring formed by the joinder of substituents carried by the imino carbon atom. Such guanidino and guanidinium embodiments of the final products I are conveniently obtained by N-derivatization of the corresponding amino embodiments according to procedures disclosed in U.S. Pat. No. 4,194,047 as was explained under 8. above. Such guanidino embodiments are also conveniently prepared directly following the procedure described in co-pending, commonly assigned U.S. patent application Ser. No. 197,865 filed Oct. 17, 1980, which application is incorporated herein by reference. It should be noted that the cited application is directed to 1-carbadethia-penems, but that the disclosed process is useful by analogy. Representatively preferred values for $R^1$ and $R^2$ attached to the carbon atom include:

H,
$CH_3$,
$CH_2CH_3$,
$CH_2OH$,
$OCH_3$,
$CH_2NH_2$,
F,
phenyl,
$CF_3$,
$CH(CH_3)_2$,
$CH_2CH_2CH_3$,
$CH_2F$, benzyl, $N(CH_3)_2$ Representatively preferred values for $R^1$ and $R^2$ attached to nitrogen atoms include:

H,
$CH_3$,
$CH_2CH_3$,
$CH_2CH_2OH$,
$—(CH_2)_2—$
$—(CH_2)_3—$
$CH(CH_3)_2$
$—(CH_2)_4—$, phenyl, $CH(CH_3)_2$, $C(CH_3)_3$,
$—CH_2CH_2OCH_2CH_2—$
$OCH_3$, $NH_2$, $NHCH_3$, $N(CH_3)_2$ The following values of $HSR^8$ are also classified under the guanidino mercaptans, giving rise to the guanidino embodiments of I:

$R^8$ is:

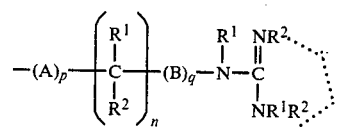

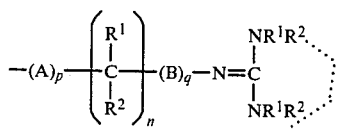

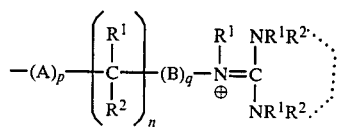

wherein $R^1$ and $R^2$ and n are as defined immediately above; p and q are 0 or 1; A and B are selected from: the aforementioned values for $R^8$ expressed in bivalent form from categories Nos. 1–7. Thus, A and B (or $—R^8—$ are selected from: cycloalkyl, alkenyl, cycloalkenyl, alkynyl (see Class No. 1 above); substituted: cycloalkyl, alkenyl, cycloalkenyl, alkynyl (see Class No. 2 above); phenyl and substitued phenyl (see Class No. 3 above); substituted and unsubstituted heteroaryl (see class No. 4, above); aryl aliphatic (see Class No. 5, above); heteroarylaliphatic, heterocyclylaliphatic, and heterocyclic (see Class No. 6, above); and alkyl-heteroatomalkyl (see Class No. 7, above); B is also selected from —O— and —NR'—.

EXAMPLES

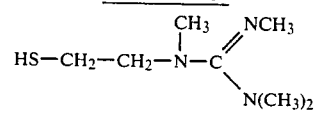

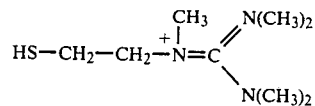

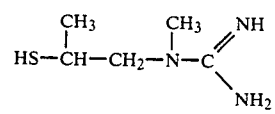

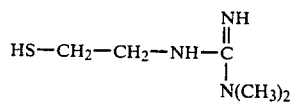

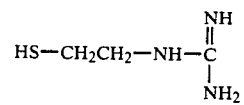

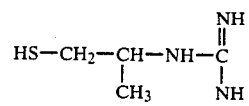

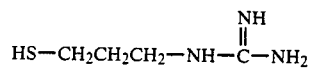

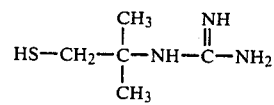

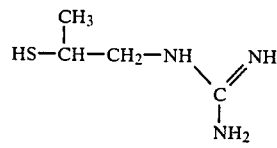

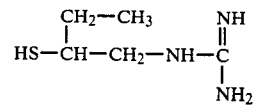

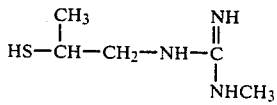

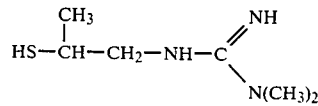

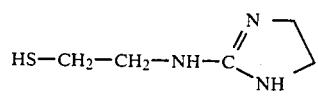

-continued
EXAMPLES

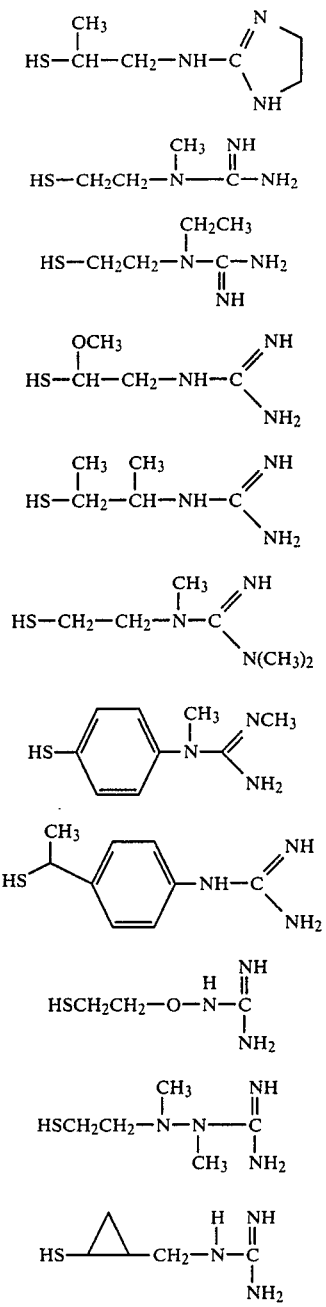

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined antibiotics, it is to be understood that there is considerable latitude in selection of precise reaction parameters. Suggestion of this latitude and its breadth is generally indicated by the enumeration of equivalent solvent systens, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total sythesis. It is to be understood that the purpose of this recitation is to further illustrate the total synthesis and not to impose any limitation. Temperature is in °C.

EXAMPLE 1

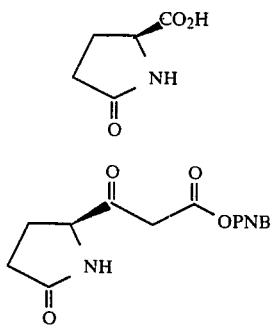

S-Pyroglutamic acid (12.9 g, 0.1 mole) was finely ground and dried in vacuo 2 days at room temperature then dissolved in a mixture of 480 ml dry tetrahydrofuran and 100 ml dry dimethylformamide. Solid 1,1-carbonyldiimidazole (17.0 g, 0.105 mole) was added in oneportion and the resulting solution stirred 1 hr at room temperature and 1 hr at 40°. The magnesium salt of mono-p-nitrobenzyl malonate (41 g, 0.0182 mole) was added. The resulting solution was stirred at room temperature for 48 hours and then concentrated to one-half volume and partioned between 500 ml ethyl acetate and 300 ml ice-cold 1m aq. hydrochloric acid. The organic phase was separated and the aqueous phase extracted with 2×200 ml ethyl acetate. The combined organics were washed with water (50 ml) and brine (200 ml), dried over sodium sulfate and evaporated to yield 25 g crude ketoester. Purification was effected by chromatography on 1000 ml silica gel with elution by a dichloromethane-ether-methanol gradient (10:10:1 to 2:2:1) to yield 21.0 g pure ketoester as a white, crystalline solid.

In an analogous manner, the following ketoester is obtained:

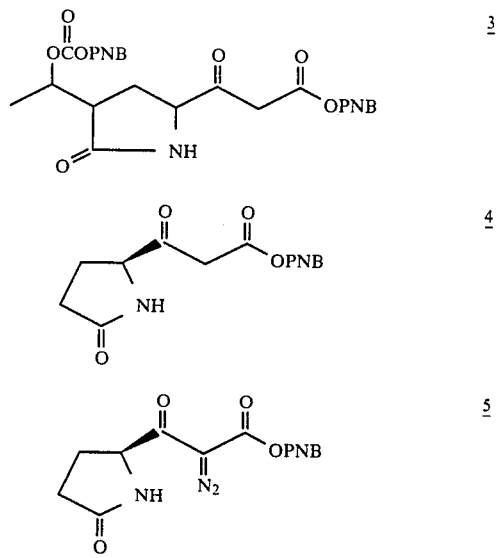

Ketoester 4 (3.9 g, 12.7 mmoles) was dissolved in 30 ml tetrahydrofuran and 60 ml acetonitrile and cooled to 0°. Triethylamine (4.2 ml, 30 mmoles) was added, followed by 2.56 g (13.0 mmoles) of p-toluenesulfonyl azide. The orange solution was stirred for 30 min at 0° then diluted with 20 ml toluene and evaporated to a gum. The crude product was purified by chromatography on 400 ml silica gel with elution by a dichloromethane-ether-methanol gradient (10:10:1 to 2:2:1) to yield 3.5 g crystalline diazoketoester 5.

Similarly prepared is diazoketoester 6:

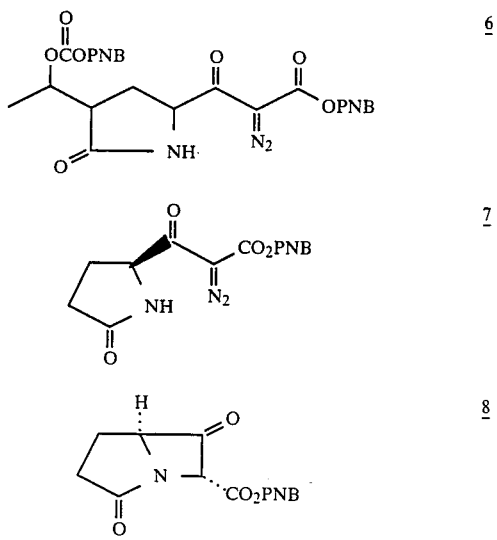

Diazoketoester 7 (1.00 g, 3.0 mmoles) was dissolved in 20 ml dry dichloromethane, 5 mg of rhodium (II) acetate was added, the mixture degassed with nitrogen and refluxed for 1 hr. Tlc revealed that the starting material had been consumed so the solvent was evaporated in vacuo with careful exclusion of atmospheric moisture. The crude product was 90% pure by 'H NMR and was used directly in the next step.

Similarly prepared is the bicyclicketoester 9:

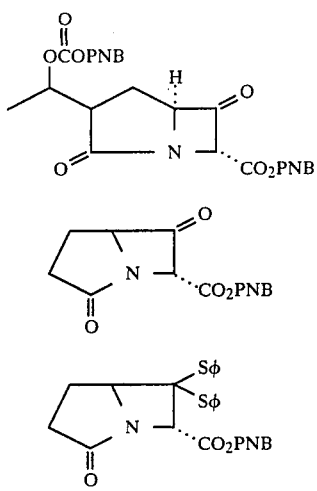

Bicyclicketoester 10 (derived from 1.00 g diazo compound 7 3.0 mmoles) was dissolved in 10 ml dry tetrahydrofuran and 20 ml dry acetonitrile and cooled to −60°. This solution was treated with 0.45 ml (3.0 mmoles) 1,8-diazabicyclo[5.4.0]undec-7-ene, aged 10 min at −60° and then treated with 0.621 ml (3.0 mmoles) diphenylchlorophosphate. The mixture was allowed to warm to −20° over 90 min and then recooled to −70°. Benzenethiol (0.560 ml, 5.0 mmoles) and diisopropylethylamine (0.87 ml, 5.0 mmoles) were added and the solution allowed to warm to 10° over 2 hrs. The reaction mixture was diluted with 100 ml chloroform, quenched with 10 ml pH 4 phosphate buffer and subjected to the usual aqueous workup followed by chromatography on 100 ml silica gel with 5–15% ethylacetate-dichloromethane gradient as eluant to yield 670 mg thioketal 11.

In an analogous manner the thioketal 12 is obtained:

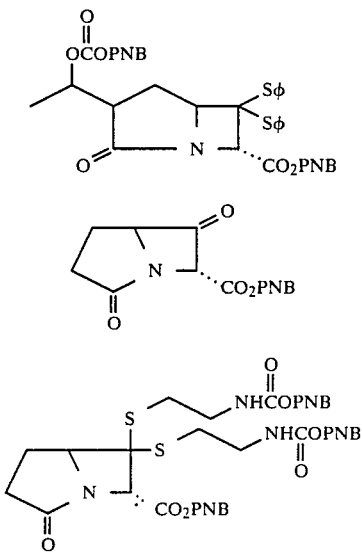

Bicyclic ketoester 13 (derived from 500 mg diazo compound, 1.5 mmoles) was dissolved in 10 ml THF and 15 ml acetonitrile and cooled to −55°. The solution was treated with 224 μl (1.5 mmoles) of 1,8-diazabicyclo[5.4.0]undec-7-ene, aged 10 min of −55° and then 310 μl (1.5 mmole) of diphenylchlorophosphate was added. The solution was allowed to warm to −20° over 90 min. then recooled to −70° and a solution of N-(p-nitrobenzyloxycarbonyl)cysteamine (800 mg, 3.0 mmoles) in 2.0 ml acetonitrile and 435 μl of diisopropylethylamine were added. The mixture was allowed to warm to room temperature over one hour then diluted with 50 ml chloroform, quenched with 25 ml pH 4 phosphate buffer and subjected to the usual aqueous workup to yield 1.35 g crude product. Purification was effected by chromatography on 80 ml of silica gel with a 10–60% ethylacetate-dichloro-methane gradient as eluant to yield 350 mg thioketal 14.

In an analogous manner the thioketal 15 is obtained:

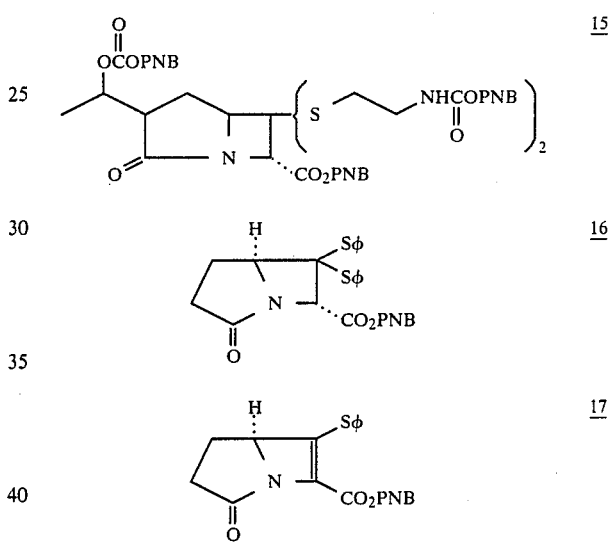

Bicyclicthioketal 16 (506 mg, 1.0 mmole) was dissolved in 10 ml dichloromethane and cooled to −20°. A solution of 210 mg (1.02 mmole) based on 85%) m-chloroperbenzoic acid in 2.0 ml dichloromethane was added dropwise over 2 min and the solution stirred 30 min at −20°. The reaction was quenched with 20 ml 10% aq. potassiumbicarboate containing a small amount of sodium sulfite diluted with 100 ml chloroform and subjected to the usual aqueous workup to yield 565 mg crude sulfoxide. The sulfoxide was dissolved in 20 ml dichloromethane and treated with 168 μl (1.2 mmole) of diisopropylamine and 150 μl (1.0 mmole) of 1,8-diazabicyclo[5.4.0]undec-7-ene. The solution was stirred at room temperature for 1 hr. then diluted with 50 ml of chloroform and washed with 2×5 ml pH 4 phosphate buffer. The organic phse was dried over sodium sulfate and evaporated and the crude product purified by chromatography on 50 ml silica gel with a 3–10% ethylacetate-dichloromethane gradient as eluant to yield 323 mg pure olefin 17.

In an analogous manner the following olefins are prepared:

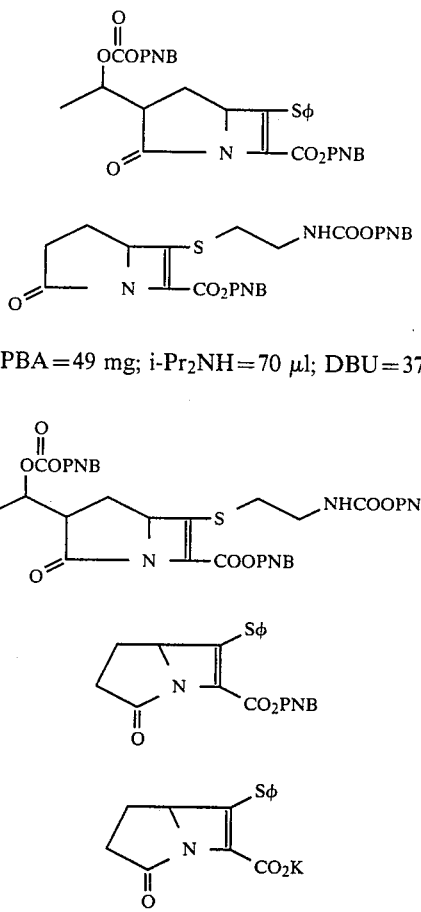

[MCPBA=49 mg; i-Pr2NH=70 μl; DBU=37μl.]

To a solution of 79 mg (0.199 mmole) of olefin 21 in 8 ml tetrahydrofuran was added 0.8 ml ethanol 4.0 ml 0.1M pH 7 phosphate buffer and 80 mg 10% palladium on charcoal and the mixture was hydogenated at 50 psi for 90 min. The reaction mixture was filtered through a small charcoal pad on celite and the residue washed with 2×2 ml water. The combined filtrates were adjusted to pH 7 with buffer and washed with 2×10 ml ether. The remaining aqueous phase was briefly concentrated in vacuo to remove organic solvents and then applied to 3 0.5 mm Analtech reverse-phase tlc plates, which were developed with 5% tetrahydrofuran in water at 5°. The major UV active band was eluted with 2:1 acetonitrile water, the eluate concentrated to ⅓ volume in vacuo (20°, 1 mm) and then lyophilized to yield 48 μmoles of olefin potassium salt by UV.

An exactly analogous procedure was used to deblock 50 mg of olefin (R$^8$=SCH2CH2NHCO2PNB) to olefin potassium salt 23 (R$^8$=SCH2CH2NH2); 15 mg (by UV). [THF 5.0 ml, ethanol 1.5 ml, H2O 1.5 ml, pH 7 phosphate 0.2 ml, 50 mg Pd/C]

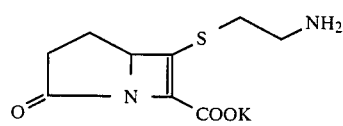

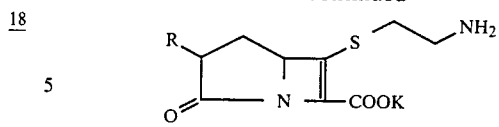

Following the above deblocking procedure, the following final product salts are obtained when the indicated substitution of starting materials is made:

R = CH3CH(OH)—

= CF3CH(OH)—

EXAMPLE 2
Step A

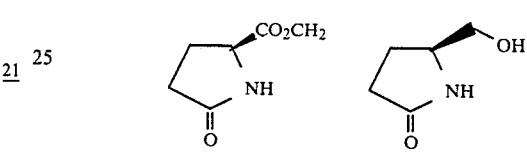

A solution of 12.0 g (0.084 mole) S-pyroglutamic acid methylester in 125 ml dry methanol at 0° was treated with 3.18 g (0.084 mole) of sodium borohydride. The internal temperature rose to 30° and the mixture was stirred at room temperature for 30 min. The solution was then quenched with 20 ml (0.336 mole) of acetic acid and concentrated to a thick gum (30°, 1 mm). The residual solid was triturated with 150 ml warm dichloromethane, filtered, and the solid washed with 50 ml dichloromethane. The filtrate was concentrated and filtered through 100 ml silica gel with 750 ml 20% methanol in dichloromethane. The eluate was concentrated and the residual semicrystalline mass was recrystallized from etherdichloromethane to yield 9.0 g white crystalline alcohol.

Step B

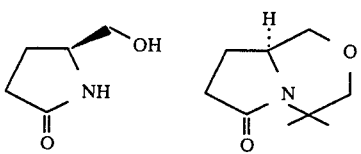

The alcohol from Step A (4.15 g, 0.036 mole) was dissolved in a mixture of 6.15 ml 2,2-dimethoxypropane and 50 ml dry benzene and 50 mg p-toluene-sulfonic acid was added. The mixture was stirred at room temperature for 48 hours and then refluxed under a Soxhlet extractor containing CaH2 for 5 hours to complete the reaction. The mixture was cooled to room temperature, washed with aqueous potassium carbonate, dried over potassium carbonate and evaporated to yield 7.2 g crude product which was purified by chromatography on 200 ml silica gel packed in 20:5:0.5 dichloromethane-ether-methanol and elution with a gradient from 20:5:0.5 to 10:10:1 afforded 5.2 g white, crystalline product.

Step C

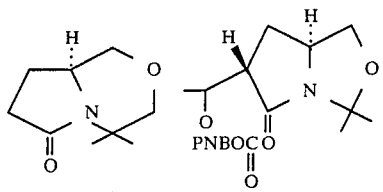

To a solution of 22 mmoles of lithium diisopropylamide in 50 ml tetrahydrofuran at −78° was added dropwise a solution of the acetonide of Step B (3.10 g, 20.0 mmoles) in 10 ml tetrahydrofuran over 10 min. The solution was aged 10 min at −78°, then quenched with 2.0 ml dry acetaldehyde. The mixture was allowed to warm to 0° and then diluted with 50 ml pH 7 buffer and 200 ml chloroform. The organic layer was separated, washed with cold dilute hydrochloric acid and aqueous potassium bicarbonate, dried over sodium sulfate and evaporated to yield 4.10 g crude alcohol mixture. This material was dissolved in 30 ml dichloromethane, 3.05 g (25 mmoles) 4-dimethylaminopyridine added followed by a solution of 4.30 g (20 mmoles) of p-nitrobenzylchloroformate in 10 ml dichloromethane. After 3 hours the salts were filtered and the filtrate diluted with dichloromethane, washed with pH 4 buffer, aqueous potassium bicarbonate and brine, dried over sodium sulfate and evaporated to yield 9.5 g crude esters which was a mixture of two major trans isomers and two minor cis isomers. The mixture was separated by HPLC to yield 3.6 g trans R*, 3.2 g trans S*, 0.6 g cis R* and 0.3 g cis S*.

Step D

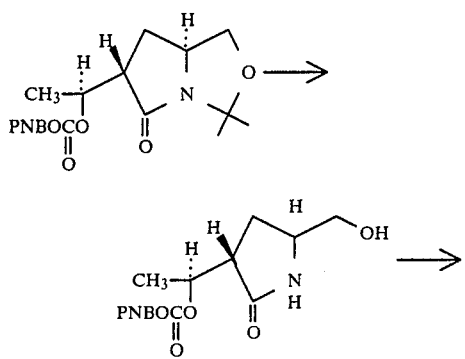

Trans R* from Step C (3.77 g, 10.0 mmoles) was dissolved in 100 ml 9:1 methanol-water and 2 g of Dowex-50 (H+) resin was added. The suspension was stirred until no starting material was visible in the tlc (6 hours) and then the resin was filtered and washed with methanol. The combined filtrates were dried over sodium sulfate and evaporated to yield 3.4 g almost pure alcohol. This material was dissolved in 100 ml dichloromethane and added dropwise to 20 ml of vigorously stirred 2M chromic acid. The mixture was stirred 3 hours at room temperature at which point the oxidation was complete by tlc. The organic phase was separated, the aqueous layer was extracted with 100 ml ethyl acetate and the combined organics washed with brine, dried over MgSO4 and evaporated to yield 2.8 g crude acid, purified by recrystallization from ethyl acetate-chloroform.

EXAMPLE 3

Preparation of Pharmaceutical Compositions

One such unit dosage form is prepared by mixing 120 mg of compound A

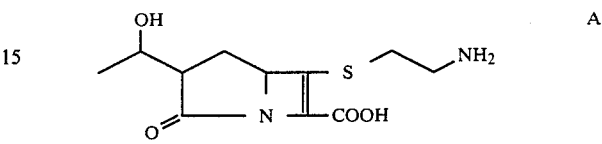

with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as com ressed tablets and pills can be prepared. The following examples are illustrative of the preparation of pharmaceutical formulations:

| TABLET | PER TABLET |
| --- | --- |
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
| --- | --- |
| PARENTERAL SOLUTION Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water to | 1 ml. |
| OTIC SOLUTION | |
| Compound A | 100 mg. |
| Benzalkonium chloride | 0.1 mg. |
| Sterile Water to | 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound of the structure:

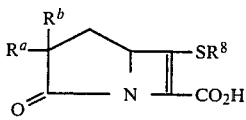

and the pharmaceutically acceptable salts and esters thereof; wherein $R^a$, $R^b$, and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl, having 5–10 ring atoms wherein the heteroatom or atoms are selected from O, S, N; wherein the substituent or substituents relative to the above-named radical values for $R^a$, $R^b$ and $R^8$ are selected from the group consisting of:

—$X^\circ$ halo (chloro, bromo, fluoro)

—OH hydroxy

—$OR^1$ alkoxy, aryloxy $$-\overset{\overset{O}{\|}}{O}CNR^1R^2 \text{ carbamoyloxy}$$

$$-\overset{\overset{O}{\|}}{C}NR^1R^2 \text{ carbamoyl}$$

—$NR^1R^2$ amino $$-N-R^1-\overset{\overset{R^2}{|}}{C}=NR^1 \text{ amidino}$$

$$-N-R^1-\overset{\overset{NR^1R^2}{|}}{C}=NR^1 \text{ guanidino}$$

—$SO_2NR^1R^2$ sulfamoyl $$-NH\overset{\overset{O}{\|}}{C}NR^1R^2 \text{ ureido}$$

$$\overset{\overset{O}{\|}}{NR^1CR^2} \text{ amido}$$

—$CO_2H$ carboxy

—$OSO_3R^1$ sulphate

—$NO_2$ nitro

—$\overset{+}{N}(R^1)_3$ ammonium ($R^1$ groups independently chosen)

$$-\overset{\overset{R^1}{|}}{C}=NOR^2 \text{ oximino}$$

—$CO_2R^1$ carboxylate $$-\overset{\overset{O}{\|}}{C}R^1 \text{ acyl}$$

$$-\overset{\overset{O}{\|}}{O}CR^1 \text{ acyloxy}$$

—SH mercapto $$-\overset{\overset{O}{\|}}{S}R^1 \text{ alkyl and aryl sulfinyl}$$

$$-\overset{\overset{O}{\|}}{\underset{\underset{O}{\|}}{S}}R^1 \text{ alkyl and aryl sulfonyl}$$

—CN cyano

—$N_3$ azido

—$SR^1$ alkyl- and arylthio $$-\overset{\overset{O}{\|}}{P}(OR^1)_2 \text{ phosphono}$$

$$-\overset{\overset{O}{\|}}{\underset{\underset{O}{\|}}{S}}OR^1 \text{ sulfo}$$

$$-NR^1\overset{\overset{O}{\|}}{\underset{\underset{O}{\|}}{S}}R^2 \text{ sulfonamido}$$

wherein, relative to the above listed substituents on $R^a$, $R^b$, and $R^8$, the groups $R^1$ and $R^2$ are independently selected from: hydrogen, alkyl, alkenyl, and alkynyl, having from 1–10 carbon atoms; cycloalky, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroalkyl, heteroaralkyl, heterocyclyl and heterocyclyalkyl and wherein the hetero atom or atoms in the above-named heterocyclic moieties are selected from the group consisting of 1–4 oxygen, nitrogen or sulphur atoms and wherein the alkyl moieties associated with said heterocyclic moieties have 1–6 carbon atoms; additional $R^8$ substituents are:

$$-N=\overset{\overset{}{\underset{\underset{R^2}{|}}{C}}}-NR^1R^2 \text{ amidino}$$

$$-\underset{\underset{R^1}{|}}{N}-\underset{\underset{R^2}{|}}{C}=NR^1 \text{ amidino}$$

$$-\underset{\underset{R^1}{|}}{N}-\underset{\underset{R^2}{|}}{C}=\overset{+}{N}R^1R^2 \text{ amidinium}$$

$$-N=\overset{\overset{}{\underset{\underset{NR^1R^2}{|}}{C}}}-NR^1R^2 \text{ guanidino}$$

$$-\underset{\underset{R^1}{|}}{N}-\underset{\underset{NR^1R^2}{|}}{C}=NR^1 \text{ guanidino}$$

-continued

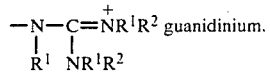

2. A compound according to claim 1 wherein $R^a$ is hydrogen; and $R^b$ is hydrogen or $CH_2CH(OH)-$; and $R^8$ is $-CH_2CH_2NH_2$.

3. An antibiotic method of treatment comprising administering a therapeutically effective amount of a compound according to claim 1.

4. An antibiotic pharmaceutical composition comprising a therapeutically effective amount of a compound according to claim 1 and a carrier therefor.

* * * * *